(12) United States Patent
Woodward

(10) Patent No.: US 6,485,441 B2
(45) Date of Patent: Nov. 26, 2002

(54) SENSORBED

(75) Inventor: Steven H. Woodward, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/821,762

(22) Filed: Mar. 28, 2001

(65) Prior Publication Data

US 2002/0007124 A1 Jan. 17, 2002

Related U.S. Application Data

(60) Provisional application No. 60/218,238, filed on Jul. 14, 2000.

(51) Int. Cl.[7] .............................................. A61B 58/00
(52) U.S. Cl. .................................................... 600/595
(58) Field of Search ................................ 600/587, 595, 600/534; 340/573.1

(56) References Cited

U.S. PATENT DOCUMENTS

| | | | |
|---|---|---|---|
| 4,320,766 A | 3/1982 | Alihanka et al. | 128/671 |
| 5,435,317 A | 7/1995 | Mcmahon et al. | 128/716 |
| 5,611,096 A | 3/1997 | Bartlett et al. | 5/617 |
| 5,684,460 A | 11/1997 | Scanlon | 340/573 |
| 5,796,340 A | 8/1998 | Miller | 340/573 |
| 5,844,488 A | 12/1998 | Musick | 340/573 |
| 5,846,206 A | 12/1998 | Bader | 600/534 |
| 5,914,660 A | 6/1999 | Mesibov et al. | 340/573 |
| 5,989,193 A | 11/1999 | Sullivan | 600/534 |
| 6,011,477 A | 1/2000 | Teodorescu et al. | 340/573.1 |

*Primary Examiner*—Max Hindenburg
(74) *Attorney, Agent, or Firm*—Lumen Intellectual Property Services, Inc.

(57) ABSTRACT

A mattress device provides a high information variety from a low number of sensors configured and placed in correspondence with a mattress core layer and a mattress top layer of the mattress device in order to monitor a patient's sleep behavior. Mattress core and top layers provide a static position transmission characteristic and a dynamic impulse transmission characteristic enabling the sensors to recognize body imprint position and body impulses induced by the sleeping patient with a broad bandwidth. In an alternate embodiment, the mattress device may be combined with a signal coder capable of receiving signals or signal components from the sensors and transform them in an analog signal that can be received and processed by a conventional sound card of a computer. A decoding program installed on the computer decodes the alphanumeric information processed from the analog signal by the sound card and makes it available for further interpretation.

16 Claims, 6 Drawing Sheets

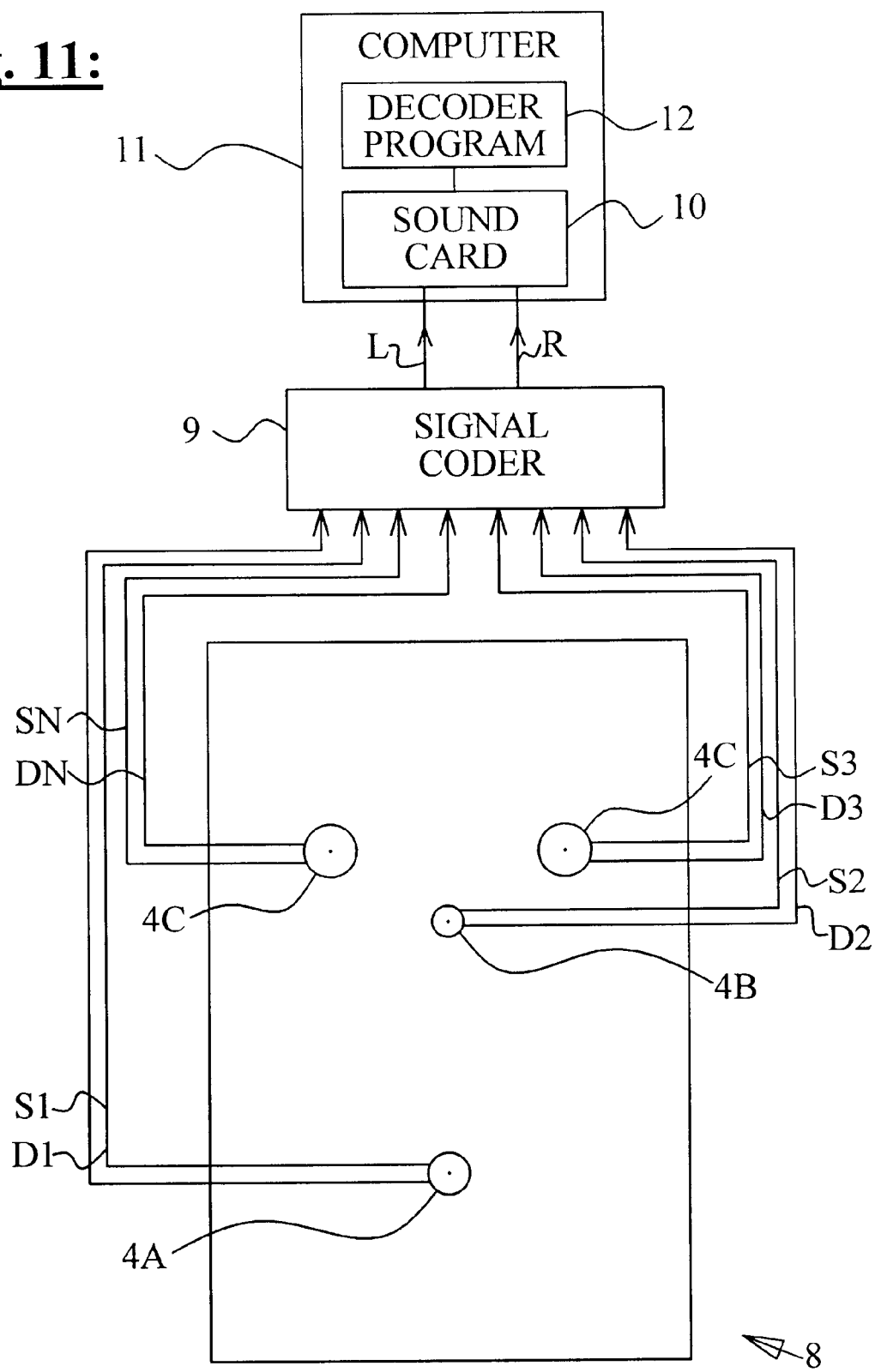

SENSORBED

RELATED APPLICATION

This application claims priority of the U.S. Provisional patent application Ser. No. 60/218,238 filed Jul. 14, 2000, which is hereby incorporated by reference.

FIELD OF THE INVENTION

This invention relates generally to sleep recording. More particularly, it relates to sleep recording without body surface sensors.

BACKGROUND OF INVENTION

Standard sleep recording or polysomnography is typically performed in a sleep laboratory using ten to twenty body-surface sensors (electrodes, elastic bands, etc.) to record various medically significant features of sleep such as electrocardiogram and respiratory movements or efforts at thorax and abdomen. The attachment of sensors using glue and tape and the routing of wires along the skin typically requires ninety minutes or more and is performed by a trained polysomnographic technician. The social context of the pre-sleep period is substantially modified and the subsequent sleeping conditions are widely acknowledged to be aberrant. Ambulatory versions of the above methodology using portable battery-powered recorders allow traditional sleep recording to be performed at a subject's home. A night of ambulatory polysomnography requires the same amount of technician time (in addition to travel time) as does sleep laboratory recording, and incurs the same discomforts associated with body-surface sensors. Though ambulatory polysomnography takes place in the home, the social context of the pre-sleep period is again modified by the extended personal interaction with the polysomnographic technician.

A number of U.S. Patents describe apparatus combined and/or integrated with mattresses in order to recognize a patient's activity during his/her sleep period.

U.S. Pat. No. 4,320,766, for example, describes a capacitive motion sensor layer placed under a mattress or the like for monitoring the movements of a person. The sensor layer is uniformly placed over the sleep area in order to recognize the person's motion, respiratory movements and heart beat during sleep. The sensor layer provides a single signal stream. Hence, the invention provides only a limited ability to derive motion information of individual body parts by filtering signal patterns from the single recorded signal. In addition, the system is only able to recognize motion and not various types of sleeping position, like for example, a stretched out or an embryonic sleeping position. In addition, the device is not suitable to make distinct measurements from abdominal and/or thorax movements.

U.S. Pat. No. 5,435,317 discloses a device for detecting a respiratory dysfunction of a person located in a bed, cot, crib or the like and for inducing a rocking motion. Four peripheral transducers are placed in a cross-like fashion within a framework designed to carry a mattress and to recognize a persons movements. The apparatus is configured to count movements rather than interpreting the nature and source of the movements. The cross like arrangement of the transducers corresponds to a mechanical movement amplification mechanism and to provide observation of the whole mattress area. The transducer positions are not defined to recognize particular body movements. The crude design of the apparatus is not suitable for a qualitative observation of sleep motion.

U.S. Pat. No. 5,611,096 discloses an apparatus for adjusting the pressures of a therapeutic mattress surface in accordance with the angular position of that surface. The apparatus comprises an angular position sensor and a rotation sensor, which are housed together in an enclosure mounted on the mattress top or the adjustable portion of the mattress supporting frame structure. The angular position sensor and the rotation sensor are configured and positioned for providing feed back of the angular mattress orientation defined by the supporting frame structure. The angular position sensor and rotation sensor are not configured to respond to a patient's movements or position.

U.S. Pat. Nos. 5,684,460 and 5,796,340 describe fluid filled sensing pads or cavities extending across a sleeping area of a mattress and being connected to transducers. The apparatus is also configured to count movements rather than interpreting the nature and source of the movements. The recognition of individual localized movements, for example, of thorax and abdominal region are limited. In addition, the volume of the sensing pad has a certain flexibility, that alters pressure information derived especially from low frequency and high amplitude impulses as they result for instance from breathing movements.

U.S. Pat. No. 5,844,488 discloses a sensor pad for installation on top and across the width of a mattress proximate the midsection of a reclining patient. The sensor pad is configured to recognize a patients movement toward an edge of the bed. The configuration includes central and edge switching areas. Hence, the sensor pad is solely able to recognize if or if not a patient is within an area defined by the switching areas' extensions. The sensor pad is not able to make qualitative interpretation of the patient's sleeping location or sleeping behavior.

U.S. Pat. No. 5,846,206 describes a method for observing the wakefulness of a vehicles driver by utilizing pressure sensor plates being in contact with the person to recognize heart beat and respiration of it. The pressure sensor plates are configured to recognize pressure related information. The patent does not disclose particular positioning or configuration of the pressure sensitive plates. Moreover, the method is mainly designed for a continuous threshold observation rather than a qualitative recording of the vehicle driver.

U.S. Pat. No. 5,914,660 describes the use of gravity switches for consistent infant observation against Sudden Infant Death Syndrome. The patent does not describe how the gravity switches are implemented or configured.

U.S. Pat. No. 5,989,193 describes the use of a pressure area sensor placed in a mattress below a patient. The sensor provides only a single signal stream with all limitations described above. In addition, the placement of the sensor beneath the mattress reduces the recording sensibility significantly, since the mattress has a major damping effect especially on high frequency and low amplitude movements like, for example, heart beat.

Finally, U.S. Pat. No. 6,011,477 describes a respiration and movement monitoring system having a mattress surface sensor and an optional accelerometer sensor attached to a mattress support platform. The mattress surface sensor has a spiral configuration and evenly covers a central sleeping area. The surface sensor recognizes respiratory movements. The uniform coverage of the sleeping area with the single surface sensor restricts the system to a movement counting rather than interpreting the nature and source of the movements. The level of recognition is limited to trigger preventive action against Sudden Infant Death Syndrome but not suitable for polysomnography.

None of the inventions described above provide the signal bandwidth necessary to retrieve sleep information compatible with clinical systems. Therefore, there exists a need for a cost effective monitoring apparatus that can be utilized for continuous sleep behavior monitoring and that does not impair a persons natural sleep or pre sleep behavior. The invention described in the following addresses this need.

SUMMARY

A mattress device for monitoring sleep behavior is introduced that may be configured as a commercially available product or be placed as an additional mattress device on top of a commercial mattress. The mattress device provides sleeping comfort compatible to that of conventional mattresses and encourages a patient to monitor his/her sleep behavior on a continuous basis. In the preferred embodiment, three monitoring regions are defined to capture relevant sleep behavior information. The monitoring regions are an abdominal region, a thorax region and a leg region. Sensors are positioned and configured in correspondence with a mattress core layer and a mattress top layer to independently recognize dynamic leg, abdominal and thorax movements with a broad signal bandwidth to capture movements ranging from heart beat or voice activity to myoclonic movements of individual body parts. In addition, the sensors respond to angular deformations of the mattress top layer induced by the patients weight.

In the preferred embodiment, the sensors are DC accelerometer sensors that have a dynamic response to motion and a static response dependent on their angular position. The dynamic response characteristic recognizes movements of a mattress core layer and a mattress top layer induced, for example, by a patient's breathing, heart beat, snoring, abdominal activity, thorax movements, limb movements and voice. The sensors are configured in conjunction with the mattress core layer for low frequency and high amplitude sensitivity across the corresponding sensing area. Low frequency and high amplitude movements may be induced on the mattress core layer, for example, by a patient's respiratory movements. The sensors are configured in conjunction with the mattress top layer for high frequency and low amplitude sensitivity across the corresponding sensing area. High frequency and low amplitude movement may be induced on the mattress top layer, for example, by a patient's heartbeat, leg movements, or voice. The mattress top layer responds similar to a membrane and may be tuned by adjusting a tensile preload of it.

The angular position of the sensors depend on the distance at which the corresponding body region imprints the mattress structure.

The sensors' response to dynamic movements and static position result in two dimensional signals of each sensor. Hence, by using three sensors, a six dimensional signal space is provided that provides information versatility at a level that is compatible with a clinical sleep behavior monitoring. Yet, the invention is simple and can be cost effective fabricated, which makes the monitoring and interpretation of sleep behavior possible for individuals on an ongoing base.

The signals derived from the sensors are collected using a data acquisition unit, which are then converted to numbers, monitored, and stored, all in a continuous fashion preserving clock time. The data acquisition unit can be a laboratory-standard software hosted in a workstation or can be specialized hardware and/or software now available for a laptop computer or any other computing device suitable of managing the data amount provided by the mattress device. An alternative is to use a signal multiplexor and a laptop equipped with a sound card. On-line or off-line digital signals analysis routines, such as bandpass filtering, but also including more advanced signal separation methods are applied to the accelerometer signals outputs to separate the components deriving from cardiac activity, respiration, body, and limb movement, body position etc. Affordable computers provide sufficient capacity to process, interpret and present the generated data amount at the time the invention was made. Standard computer features like, for example, sound processing capabilities may be utilized to process the sensor signals which may be recoded in order to have a frequency spectrum compatible to that conventionally managed by a commercial sound cards.

BRIEF DESCRIPTION OF THE FIGURES

FIG. 11 shows a schematic assembly configuration of an embodiment of the present invention including a signal coder and a decoder software.

DETAILED DESCRIPTION

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

Figure 1:
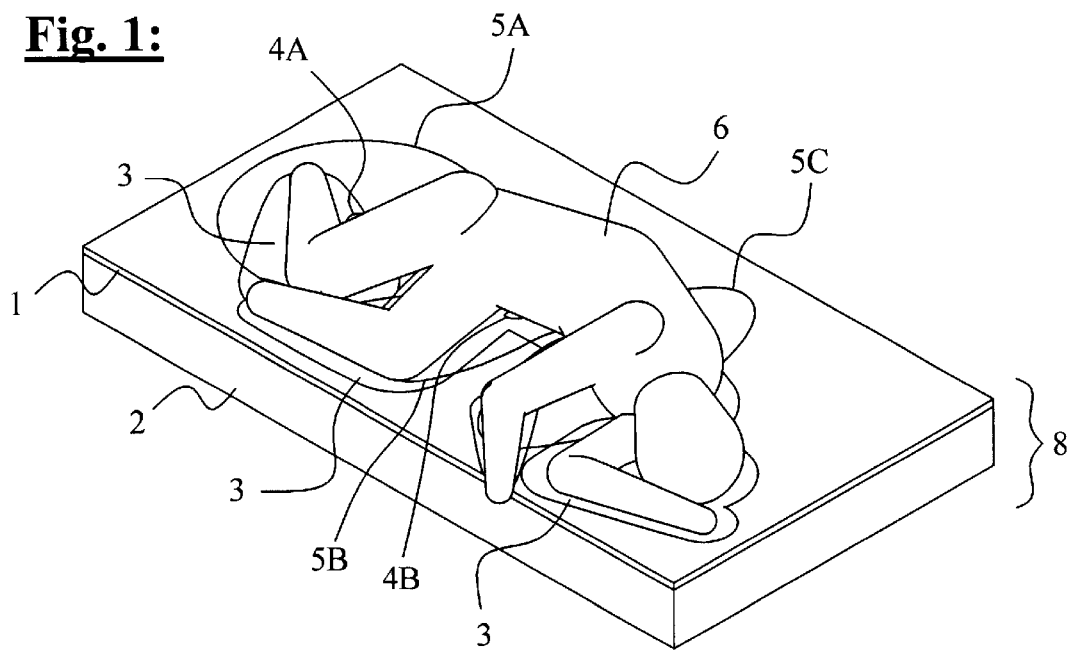
FIG. 1 shows a simplified isometric view of a patient in exemplary sleeping position on a mattress device for sleep behavior monitoring.

FIG. 1 shows a human patient 6 in exemplary sleeping position on a mattress device 8 having a mattress core layer 2 and a mattress top layer 1. Where the patient 6 directly contacts the mattress top layer 1, his or her weight produces the imprinted areas 7. Due to the elastic nature of the mattress core layer 2 and the mattress top layer 1, shoulder areas 3 are formed around the imprinted areas 7.

Figure 2:
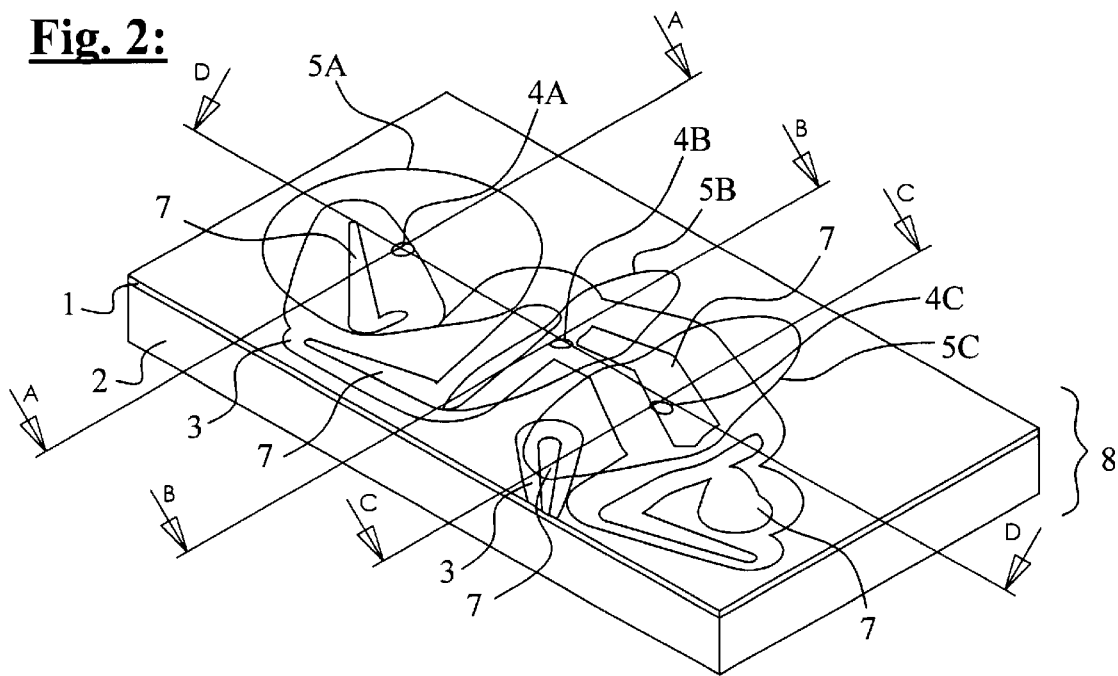
FIG. 2 shows the mattress device of FIG. 1 with imprints resulting from the patient shown in FIG. 1.

The mattress core layer 2 is preferably configured to provide a homogeneous compressive elasticity at least within sensing areas 5A, 5B, 5C (see also FIG. 2). The mattress top layer 1 is configured to provide a homogeneous tensile stiffness at least within the sensing areas 5A, 5B, 5C. The mattress core layer 2 may be, for example, foam. The mattress top layer 1 is preferably a cloth material like, for example, a spandex material. The mattress top layer 1 is configured with a tensile preload resulting in a predetermined expansion of it. The tensile preload is at a level sufficiently high to prevent waving or wrinkling of it at least within the sensing areas 5A, 5B, 5C while the patient 6 is lying on the mattress device 8.

With increasing elasticity of the mattress core layer 2 and with increasing tensile stiffness and/or tensile preload of the mattress top layer 1, the shoulder areas 3 extend further lateral from the imprinted areas 7. The shoulder areas 3 are essentially tangential and bent surfaces between the flat portion of the mattress top layer 1 and the imprinted areas 7. Hence, the further the shoulder areas 3 extend lateral from the imprinted areas 7 for a given body imprint, the larger the bending radius of the shoulder areas 3. The imprinted areas 7 have usually a mainly concave curvature induced by the body contours of the patient 6, whereas the shoulder areas 3 have a convex curvature.

The mattress core layer 2 is preferably made from homogeneous material and is configured to provide sufficient suspension for the weight of the patient 6 such that it may sleep on the mattress device 8 comfortably and at the same time provides imprint depth for a given weight range of the patient 6. The mattress top layer 1 may be configured to the particular functional needs of sensors 4A, 4B, 4C (see FIG. 2). A tensile preload may be applied in various amounts in longitudinal mattress direction and lateral mattress direction. As a result, the lateral extension of the shoulder areas 3 for a given body imprint may be directional tuned.

The elasticity and thickness of the mattress core layer 2 and the tensile stiffness and the tensile preload of the mattress top layer 1 define a static transmission characteristic of the mattress device 8, which mainly influences the lateral extension of the shoulder areas 3 for a given imprint area 7 and a given imprint depth. On the other hand, the tensile preload of the mattress top layer 1 and a damping characteristic of the mattress core layer 2 define a dynamic transmission characteristic of the mattress device 8, which influences the distance and authenticity with which mechanical impulses induced by the patient 6 are transmitted towards the sensors 4A, 4B, 4C (see FIG. 2). The static and dynamic transmission characteristic define mainly define the size and shape of the sensing areas 5A, 5B, 5C. The static and dynamic transmission characteristic may be also adjusted to different body types, sensor configurations and/or comfort levels of mattress device 8.

FIG. 2 shows the mattress device 8 with imprinted areas 7 resulting from the patient 6 in a sleeping position as illustrated in FIG. 1. In the centers of the sensing areas 5A, 5B, 5C are the sensors 4A, 4B, 4C embedded within the mattress core layer 2 and contacting the mattress top layer 1. In the preferred embodiment of the invention, three sensors 4A, 4B, 4C are used to provide a monitoring of a leg region, an abdominal region and a thorax region. The leg region corresponds to the first sensing area 5A. The abdominal region corresponds to the second sensing area 5B, and the thorax region corresponds to the third sensing area 5C. It is clear to one skilled in the art that the core of the invention is not limited to a particular number of sensing areas combined with sensors therein. Moreover, a number of sensors may be placed within a single sensing area or within two or more overlapping sensing areas.

The mattress device 8 of the present invention has the first, second and third sensors 4A, 4B, 4C in a configuration that provides information in responds to movement and to angular positioning of them. Low frequency and high amplitude movements have a static nature and travel mainly through the mattress core layer 2 resulting in a temporary angular movement combined with an oscillating acceleration of the sensors 4A, 4B, 4C. High frequency and low amplitude movements have a highly dynamic nature and travel mainly along the mattress top layer 1 that operates like a membrane. The higher the tensile preload of the mattress top layer 1 in particular direction is, the better high frequency movements travel in that particular direction. The sensing areas 5A, 5B, 5C are the areas where low and high frequency movements with high and low amplitudes are sufficiently recognizable by the central sensors 4A, 4B, 4C.

The sensors 4A, 4B, and 4C are placed within or are part of a housing that has a housing configuration in correspondence to the concave and convex curvature ranges of the imprinted areas 7 and the shoulder areas 3. In the preferred embodiment the sensor housing is snuggly embedded in the mattress core layer 2 and attached to the mattress top layer 1. Consequently, the sensors 4A, 4B, 4C recognize the angular position of the mattress top layer 1 at the location where the sensor housing is attached to the mattress top layer 1. Hence, selecting an elasticity and thickness of the mattress core layer 2, a tensile stiffness and tensile preload of the mattress top layer 1 influences the angular position of the sensors 4A, 4B, 4C, for given imprinted areas 7 and a given imprint depth.

The first sensing area 5A is configured to capture leg movements in the lower portion of mattress device 8. Leg movement may occur over an extended area in both longitudinal and lateral direction away from the center of the sensing area 5A. To the contrary, abdominal activity and thorax activity need to be captured in close longitudinal proximity over an extended lateral distance. This is, because the patient 6 moves laterally on the mattress during a sleep period. Hence, the individual sensing areas 5A, 5B, 5C are differently shaped. The first sensing area 5A may have a sensing area that extends uniformly in all direction away from its center, whereas the second and third sensing areas 5B, 5C need to extend further in lateral direction than in longitudinal direction. The mattress top layer 1 may be configured with a longitudinal and lateral tensile preload such that the shoulder areas 3 may extend laterally and longitudinally to provide angular positioning to the central sensors 4A, 4B, 4C for imprinted areas 7 that fall within the sensing areas 5A, 5B, 5C. In addition, the mattress top layer 1 may be configured with a longitudinal and lateral tensile preload such that a lateral and longitudinal dynamic transmission characteristic is defined for the mattress top layer 1 in correspondence to the shape of the sensing areas 5A, 5B, 5C. The tension of the mattress top layer 1 may be directional and/or unidirectional tuned. The tension tuning may be accomplished by wrapping mattress top layer 1 partially or completely around the mattress core layer 2 or by other features that are well known for adjusting the tension of layers within a given area.

Figure 6:
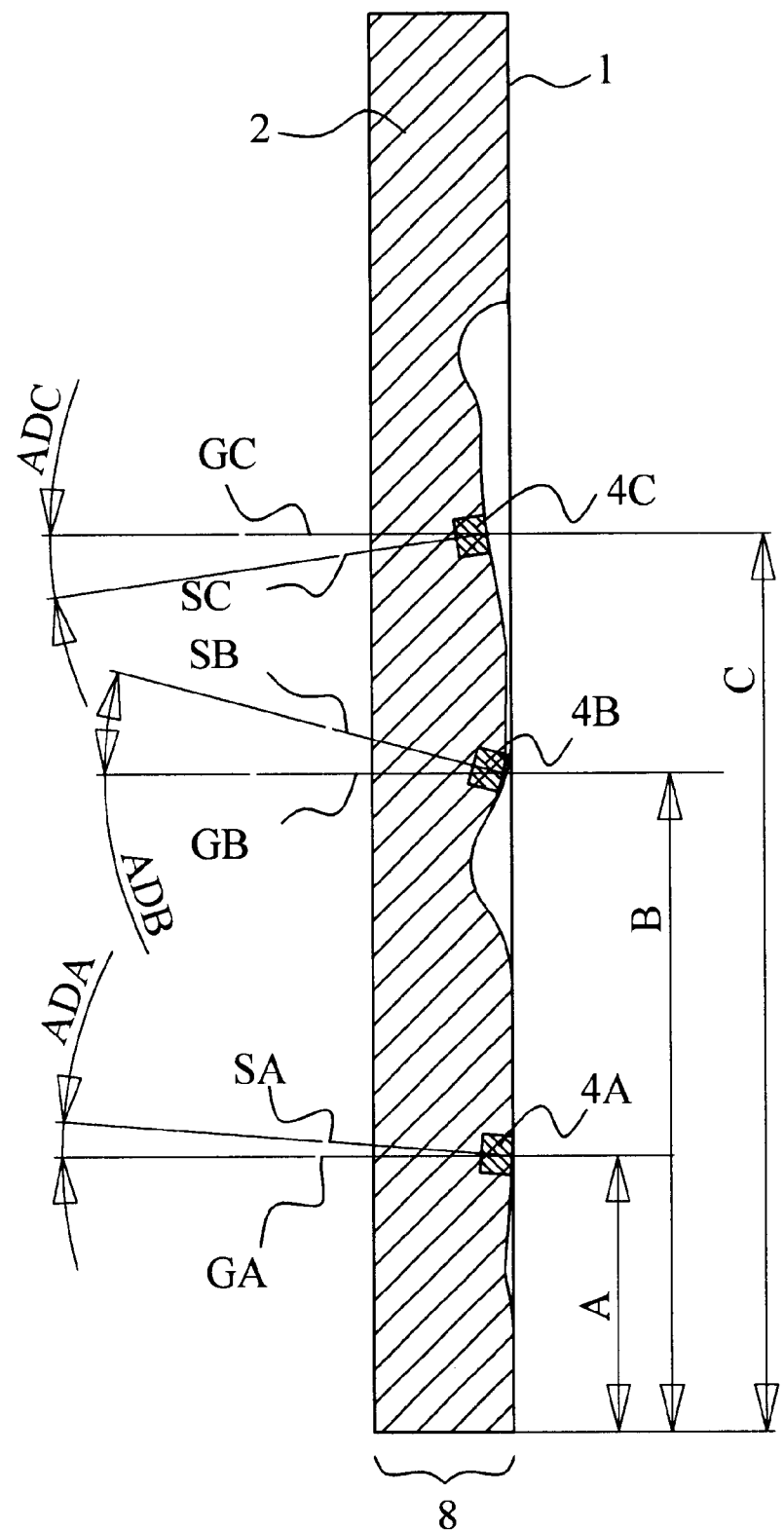
FIG. 6 shows a simplified section view in vertical orientation of the mattress device as indicated in FIG. 2 by the section line D.

FIG. 2 further shows the section lines A, B, C, D through the centers of the sensors 4A, 4B, 4C. Defining the section lines A, B, C, influences the signal space created from the individual sensors 4A, 4B, 4C. Each of the sensors 4A, 4B, 4C contributes a two dimensional signal to the signal space. The two dimensional signal has a first signal dimension that corresponds to the dynamically recognized movements and a second signal dimension that corresponds to the angular position of sensors 4A, 4B, 4C. Thus, for a mattress device 8 with the exemplary number of three sensors 4A, 4B, 4C, the signal space is six dimensional. The multi dimensional signal space changes when the section lines A, B, C are changed. The section lines A, B, C may be defined relative to the bottom edge of the mattress device 8 as shown in FIG. 6 or relative to the top edge of the mattress device since people intend to position themselves longitudinally in the bed either relative to the bottom edge of the bed or relative to the top edge of the bed. For a consistent monitoring of sleep behavior the longitudes are preferably positioned at positions with highest signal probability. This is particularly important for the abdominal and thorax monitoring regions, which are in relatively close longitudinal proximity to each other and have to recognize faint signals like, for example, heart beat.

Since the mattress top layer 1 is preferably from cloth, the mattress top layer 1 has no height assigned in the FIGS. 3–6. FIGS. 1, 2 to the contrary, illustrate the mattress top layer 1 with a thickness solely for the purpose of illustrating the presence of the mattress top layer 1 in the invention.

Figure 3:
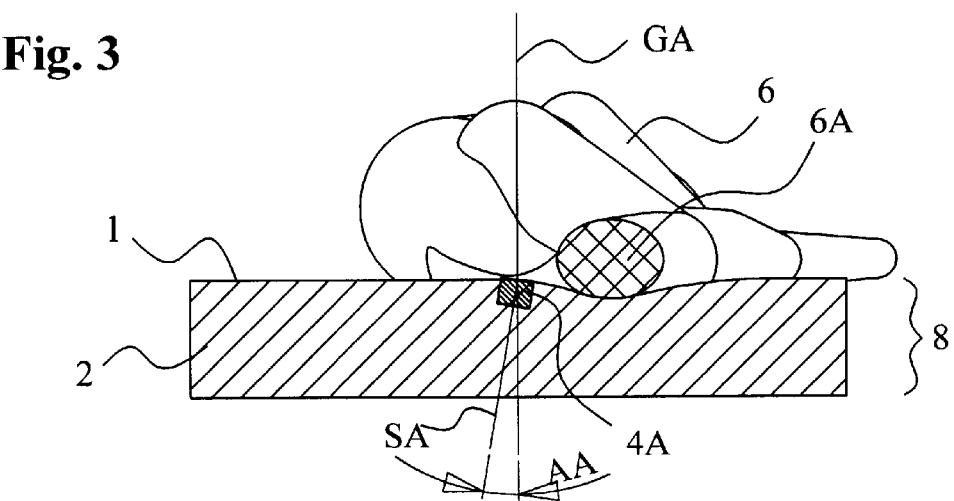
FIG. 3 shows a simplified section view of the mattress device together with the patient as indicated in FIG. 2 by the section line A.

FIG. 3 shows a section view along the lateral section line A of FIG. 2 through the center of the first sensing area 5A and the sensor 4A, which corresponds to the leg monitoring region of the preferred embodiment of the invention. A patient's leg is shown with its section view 6A where it imprints the mattress top layer 1 and the mattress core layer 2. Due to the imprint of the leg, the first sensor 4A is with its first sensor axis SA brought into a first lateral angle AA relative to a first reference axis GA.

Figure 4:
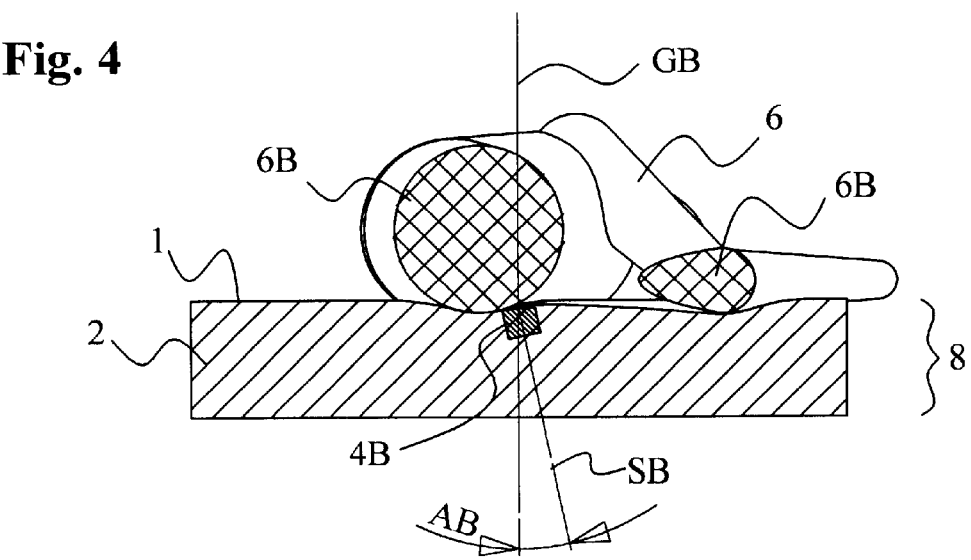
FIG. 4 shows a simplified section view of the mattress device together with the patient as indicated in FIG. 2 by the section line B.

FIG. 4 shows a section view along the lateral section line B of FIG. 2 through the center of the second sensing area 5B and the second sensor 4B, which corresponds to the abdominal monitoring region of the preferred embodiment of the invention. A patient's abdominal region is shown with its section view 6B where it imprints the mattress top layer 1 and the mattress core layer 2. Due to the imprint of the abdominal region, the second sensor 4B is with its second sensor axis SB brought into a second lateral angle AB relative to a second reference axis GB.

Figure 5:
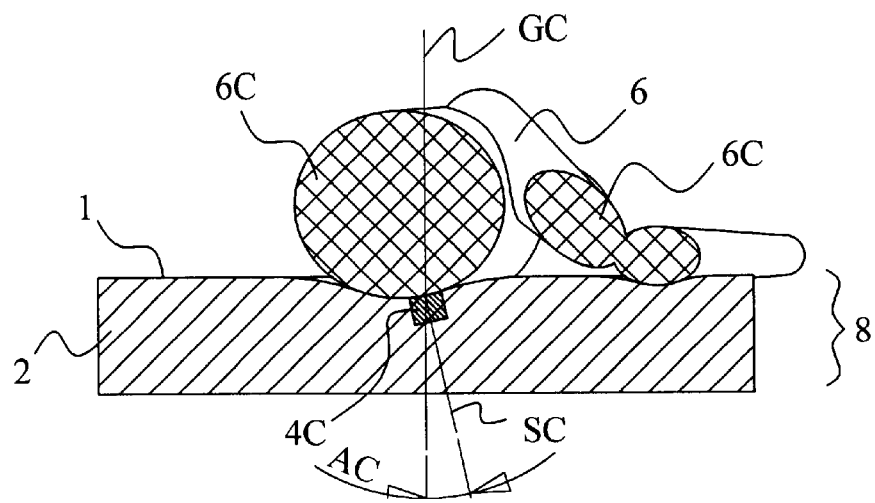
FIG. 5 shows a simplified section view of the mattress device together with the patient as indicated in FIG. 2 by the section line C.

FIG. 5 shows a section view along the lateral section line C of FIG. 2 through the center of the third sensing area 5C and the third sensor 4C, which corresponds to the thorax monitoring region of the preferred embodiment of the invention. A patients thorax region is shown with its section view 6C where it imprints the mattress top layer 1 and the mattress core layer 2. Due to the imprint of the thorax region, the third sensor 4C is with its third sensor axis SC brought into a third lateral angle AC relative to a third reference axis GC.

FIG. 6 shows a section view in vertical orientation along the longitudinal section line D of FIG. 2 through the centers of first, second and third sensing areas 5A, 5B, 5C and first, second and third sensors 4C. For the purpose of simplicity, only the imprint of the patient 6 on the mattress top layer 1 and the mattress core layer 2 are shown in FIG. D—D. The first sensor 4A is brought by the patients's imprint into a first longitudinal angle ADA relative to the first reference axis GA. The second sensor 4B is brought by the patient's imprint into a second longitudinal angle ADB relative to the second reference axis GB. The third sensor 4C is brought by the patient's imprint into a third longitudinal angle ADC relative to the third reference axis GC.

The longitudinal angles ADA, ADB, ADC combined with their corresponding lateral angles AA, AB, AC result in first, second and third true spatial angles, which reflect the maximal twist of the sensors 4A, 4B, 4C relative to their reference axes GA, GB, GC. The reference axes GA, GB, GC represent the orientation of the sensor axes SA, SB, SC without being twist by a patient's imprint.

In the preferred embodiment of the invention, the sensors SA, SB, SC are DC accelerometer sensors balanced to the natural earth gravitation in vertical orientation to provide a calibrated reference resistance in vertical immobile position. The DC accelerometer sensors impose a resistance to an induced DC Voltage in response to an acceleration induced to them along their sensor axes SA, SB, SC. The DC accelerometer sensors become misbalanced, once they are brought out of their vertical balanced orientation resulting in a change of a static resistance of them. The DC accelerometer sensors continue to respond to induced acceleration in twisted orientation and dynamically change their resistance above and below their static resistance.

Figure 7:
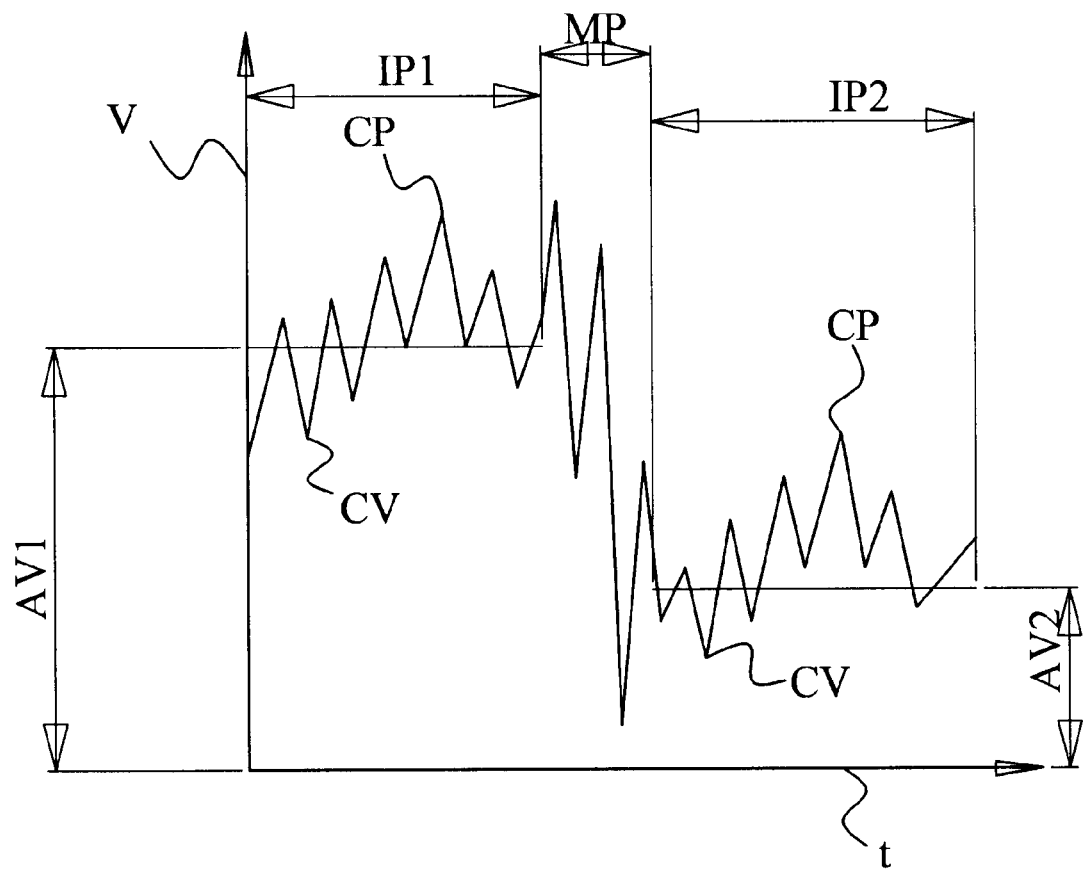
FIG. 7 shows an exemplary signal graph for a sensor of the mattress device.

FIG. 7 shows a simplified graph of a voltage signal resulting from static and dynamic resistance changes. The vertical axis V represents the voltage level of the signal and the horizontal axis t represents the elapsed time. The exemplary voltage signal is solely illustrated for the purpose of general understanding without any claim of accuracy.

During a first immobility period IP1 the patient 6 may maintain a defined sleeping position resulting in a first static resistance in one of the sensors 4A, 4B, 4C and consequently in a first average signal voltage level AV1. Other events like, for example, heart beat or respiratory movement may be recognized by one of the sensors 4A, 4B, 4C resulting in dynamic resistance changes and consequently in dynamic changes of the signal voltage. This is illustrated in FIG. 7 by the curve peaks CP and the curve valleys CV.

During a movement period MP, the patient 6 may change his sleeping position with one of the sensing areas 5A, 5B, 5C resulting in a changing twist of one of the sensors 4A, 4B, 4C. After the patient 6 has come to rest in a different sleeping position, a second average voltage level AV2 is generated with the curve peaks CP and the curve valleys CV being newly leveled relative to the second average voltage level AV2. Hence, each of the sensors 4A, 4B, 4C provides a two dimensional signal; one signal dimension for dynamic movements as they are well known to those skilled in the art and one signal dimension for static position changes of the patient 6. Hence, the mattress device 8 provides an information variety that rises more than proportional with the number of used sensors. This means for the preferred embodiment where three sensors 4A, 4B, 4C are used, that a six dimensional signal space is provided through three signal lines.

It is clear to one skilled in the art that the core of the invention extends to embodiments where sensors are placed at other locations that may be suitable for capturing and monitoring sleep behavior. Sensors may be placed additionally or exclusively along a lateral axis rather than a longitudinal axis as is described for the preferred embodiment. For example, the thorax region and/or the abdominal region may be covered by two or more lateral sensors rather than one central in order to provide a larger lateral extension of the second and/or third sensing areas 5B, 5C.

In another embodiment, the mattress device 8 may be combined with a facial device that keeps an additional sensor in close proximity to the nostrils and the mouth region of the patient 6 in order to capture respiratory movement, teeth grinding and/or voice activity. The sensor may be combined with a fluid filled pad snuggly contacting at least one eye of the patient 6 in order to capture eyelid movements or movements of the eye beneath the closed lid. The sensor may be a conventional transducer or a sensor capable of recognizing angular position changes as described for the sensors 4A, 4B, 4C such that it may also utilized to directly recognize head movements.

The signals provided by the sensors may be directed to any control unit for recording, filtering, processing, interpreting and/or presenting the information derived from the mattress device 8 together with eventual assisting sleep monitoring devices like, for example, the facial device.

It is clear that the core of the invention is not limited to the use of DC accelerometer sensors. Any sensor or combination of individual sensors for recognizing angular positioning and acceleration or mechanical impulses may be utilized within the scope of the invention. For example, inclinometers may be incorporated in the sensors 4A, 4B, 4C for recognizing the angular orientation of the sensors 4A, 4B, 4C during their operational use. In another example, transducers configured for receiving or excerpting acoustic signals may be utilized in order to recognize mechanical impulses induced by the person lying on the mattress device 8.

Figure 8:
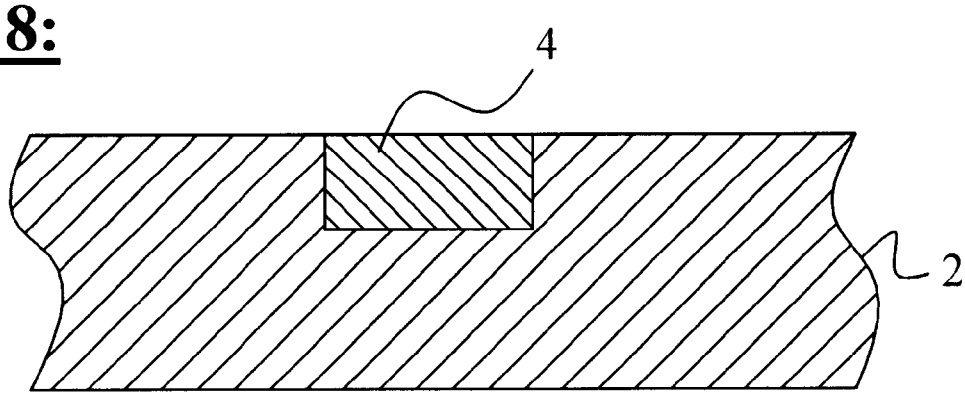
FIG. 8 shows a simplified cross section of a first exemplary assembly configuration of a sensor in the mattress device.
Figure 9:
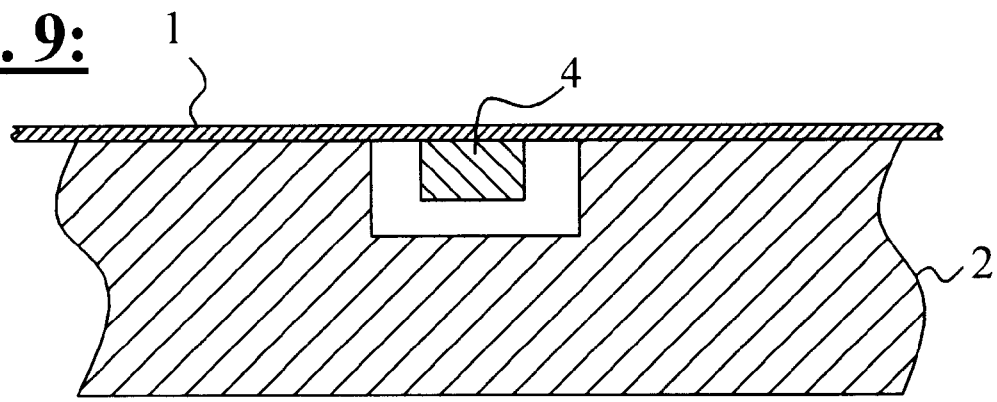
FIG. 9 shows a simplified cross section of a second exemplary assembly configuration of a sensor in the mattress device.
Figure 10:
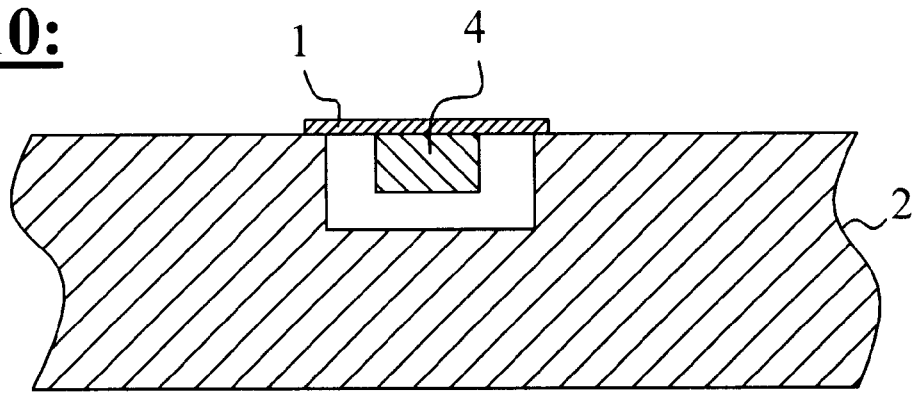
FIG. 10 shows a simplified cross section of a third exemplary assembly configuration of a sensor in the mattress device.

FIGS. 8, 9, 10 show various basic assembly configurations of the sensors 4A, 4B, 4C in the mattress device 8. Each assembly configuration may be utilized in order to assist the sensors 4A, 4B, 4C to recognize the signals relevant for the purpose of sleep behavior recognition as is well known to those skilled in the art.

In FIG. 8, the sensor 4, which corresponds to one of the sensors 4A, 4B, 4C is directly contacting the mattress core layer 2 such that the transmission characteristic of the mattress core layer 2 is directly utilized. A mattress top layer 1 (not shown in FIG. 8) may or may not be additionally utilized. As a result, the sensor 4 recognizes primarily signals that are able to pass through the mattress core layer 2. Such signals may have low frequency and high amplitude, like for example thorax movements.

In FIG. 9, the sensor 4 is in no direct contact with the mattress core layer 2 and only attached to the mattress top layer 1 extending over at least one of the sensing areas 5A, 5B, 5C. As a result, signals with a medium frequency and medium amplitude may be primarily recognized by the sensor 4 within one of the sensing areas 5A, 5B, 5C. Such medium frequency signals may be but are not limited to, for example foot and leg movements and arm, hand or finger movements.

In FIG. 10, the sensor 4 is in no direct contact with the mattress core layer 2 and only attached to the mattress top layer 1, which has a lateral extension essentially configured for bridging over the gap between the sensor 4 and the mattress core layer 2. In this configuration, the mechanical signals with high frequency and low amplitude are preferably passed on to the sensor 4. Due to the minimized contact of the mattress top layer 1 with the mattress core layer 2, signal attenuation resulting from the damping mass of the mattress core layer 1 is kept to a minimum. In addition, signal separation between individual sensors 4A, 4B, 4C may be maximized. In the assembly configuration represented in FIG. 10, the mattress top layer 1 is preferably configured in correspondence to the weight of the sensor 4 and/or the lateral stiffness and strength of the mattress core layer 2. For example, for a high strength and stiffness of the mattress core layer 2 and a low weight of the sensor 4, the mattress top layer 1 may be of material layer incapable of holding its shape without being brought under tension by being fixated on the mattress core layer 2. On the other extreme, the mattress top layer 1 may be of a configuration suitable to hold the sensor 4 in operational position without being brought under tension. The material top layer 1 according to the embodiment of FIG. 10 is configured in order to provide the flexibility to snuggly adjust to a persons body contours contacting the material top layer 1. The material top layer 1 according to the embodiment of FIG. 10 has a resilience sufficient to receive high frequency and low amplitude signals excerpted by the persons as is well understood by one skilled in the art.

FIG. 11 shows an alternate embodiment of the present invention, in which a signal coder 9 is provided to transform the dynamic signals D1–DN and the static signals S1–SN received from sensors 4A, 4B, 4C. The transformation is performed in accordance to a recording bandwidth of a conventional sound card 10 of a computer 11. A conventional sound card 10 may have input channels L, R for receiving analog acoustic signals as is well known to those skilled in the art. In the case where the sound card 10 is a regular component of a commercially available computer 11, the signal coder 9 enables a user of the mattress device 8 to connect the mattress device 8 directly to the computer 11. In that case, a decoder software 12 may be installed on the computer 11 in order to decode accordingly the alphanumeric information generated by the sound card 10 from the received coded signals received via the signal channels L, R. The decoded alphanumeric information is an alphanumeric representation of the signals S1–SN and D1–DN. As a result, any owner of a computer 11 having a sound card 10 may be able to connect the mattress device directly to his/her computer 11 and operate it after installing the decoder software 12.

The signal coder 9 is any device as is well known to those skilled in the art suitable to receive a number of individual analog or digital signals as represented by the signals S1–SN and D1–DN and to transform them into analog signals in fashion that corresponds to the signal characteristic of conventional signals received by a sound card 10 during is intended use as a sound signal processing device.

Accordingly, the scope of the invention described in the specification above is set forth by the following claims and their legal equivalent:

What is claimed is:

1. A mattress device for monitoring sleep behavior comprising:
   a) a mattress core layer;
   b) a mattress top layer;
   c) a dynamic response means placed in correspondence with said mattress core layer for creating a dynamic response signal in response to a mechanical impulse induced by a patient lying on said mattress device; and
   d) a static response means placed in correspondence with said mattress core layer for creating a static response signal in response to an angular position change induced by said patient imprinting said mattress device, wherein said dynamic response means and said static response means are combined in a sensor and said dynamic response and static response signal contribute to a signal space for evaluating said sleep behavior.

2. A system for monitoring sleep behavior comprising:
   a) a mattress core layer;
   b) a mattress top layer;
   c) a dynamic response means placed in correspondence with said mattress core layer for creating a dynamic response signal in response to a mechanical impulse induced by a patient lying on said mattress device;

d) a static response means placed in correspondence with said mattress core layer for creating a static response signal in response to an angular position change induced by said patient imprinting said mattress device, wherein said dynamic response means and said static response means are combined in a sensor and said dynamic response and static response signal contribute to a signal space for evaluating said sleep behavior;

e) a signal coder for receiving said dynamic response signal and said static response signal and for transforming said dynamic response signal and said static response into an analog signal recognizable by a sound card; and f) a decoder program for decoding an alphanumeric information in accordance with said transforming, said alphanumeric information being computed by said sound card from said analog signal.

3. The mattress device of claim 1 or 2, wherein said sensor is an accelerometer, said accelerometer providing a DC signal component in correspondence to said angular position change and an analog signal component corresponding to said mechanical impulse.

4. The mattress device of claim 1 or 2, wherein said mattress device comprises a sensing area for receiving said mechanical impulses and for transmitting said mechanical impulses towards said dynamic response means.

5. The mattress device of claim 4, wherein said sensing area is a thorax monitoring area.

6. The mattress device of claim 4, wherein said sensing area is an abdominal monitoring area.

7. The mattress device of claim 4, wherein said sensing area is a leg monitoring area.

8. The mattress device of claim 2, wherein said decoder program is stored on a data storage medium.

9. The mattress device of claim 2, wherein said data storage medium is a floppy disk.

10. The mattress device of claim 2, wherein said data storage medium is a compact disk.

11. The mattress device of claim 2, wherein said decoder program is a self extracting data string accessible for down loading from a web page.

12. The mattress device of claim 2, wherein said decoder program is a self extracting email attachment.

13. A method for providing a sleep behavior information of a patient sleeping on a mattress device, said method comprising the steps of:

a) receiving an impulse and a static body imprint from said patient induced on said mattress device during said sleeping;

b) dynamically transmitting said impulses to a sensor means;

c) inducing an angular position change to said sensor means from said body imprint;

d) transforming said transmitted impulse within said sensor means into a impulse response signal component; and e) transforming said angular position change within said sensor means into a twist response signal component.

14. The method of claim 13 further comprising the steps of combining said impulse response signal component and said twist response signal component into a multi dimensional sleep behavior signal.

15. The method of claim 14, wherein said multi dimensional sleep behavior signal is transformed in an analog signal recognizable by a sound card.

16. The method of claim 15 further comprising the step of decoding an alphanumeric information in accordance with said transforming in an analog signal, said alphanumeric information being computed by said sound card from said analog signal.

* * * * *